US009223051B2

(12) United States Patent
Bendahan

(10) Patent No.: US 9,223,051 B2
(45) Date of Patent: *Dec. 29, 2015

(54) X-RAY BASED SYSTEM AND METHODS FOR INSPECTING A PERSON'S SHOES FOR AVIATION SECURITY THREATS

(71) Applicant: Rapiscan Systems, Inc., Torrance, CA (US)

(72) Inventor: Joseph Bendahan, San Jose, CA (US)

(73) Assignee: Rapiscan Systems, Inc., Torrance, CA (US)

( * ) Notice: Subject to any disclaimer, the term of this patent is extended or adjusted under 35 U.S.C. 154(b) by 44 days.

This patent is subject to a terminal disclaimer.

(21) Appl. No.: 14/149,473

(22) Filed: Jan. 7, 2014

(65) Prior Publication Data

US 2014/0185755 A1      Jul. 3, 2014

Related U.S. Application Data

(63) Continuation of application No. 12/948,738, filed on Nov. 17, 2010, now Pat. No. 8,654,922.

(60) Provisional application No. 61/313,772, filed on Mar. 14, 2010, provisional application No. 61/262,176, filed on Nov. 18, 2009.

(51) Int. Cl.
*G01V 5/00* (2006.01)
*G01V 3/10* (2006.01)
*G01N 23/10* (2006.01)

(52) U.S. Cl.
CPC *G01V 5/005* (2013.01); *G01V 3/10* (2013.01); *G01V 3/104* (2013.01); *G01V 5/0008* (2013.01); *G01V 5/0016* (2013.01); *G01V 5/0025* (2013.01); *G01N 23/10* (2013.01); *G01N 2223/639* (2013.01)

(58) Field of Classification Search
CPC ... G01N 23/04; G01N 23/083; G01N 23/087; G01N 23/10; G01N 2223/04; G01N 2223/1006; G01N 2223/3301; G01N 2223/3303; G01N 2223/41; G01N 2223/423; G01N 2223/639; G01V 5/0008; G01V 5/0016; G01V 5/0033; G01V 5/0041; G01V 5/0066; G01T 7/12
See application file for complete search history.

(56) References Cited

U.S. PATENT DOCUMENTS

| | | | | |
|---|---|---|---|---|
| 3,790,799 A * | 2/1974 | Stein et al. | | 378/146 |
| 7,016,473 B1 * | 3/2006 | Linev et al. | | 378/146 |
| 7,561,666 B2 * | 7/2009 | Annis | | 378/87 |
| 7,796,734 B2 * | 9/2010 | Mastronardi et al. | | 378/90 |
| 8,275,093 B2 * | 9/2012 | Rothschild | | 378/62 |
| 8,654,922 B2 * | 2/2014 | Bendahan | | 378/63 |
| 2007/0211922 A1 * | 9/2007 | Crowley et al. | | 382/115 |
| 2011/0026674 A1 * | 2/2011 | Rothschild | | 378/57 |
| 2011/0129063 A1 * | 6/2011 | Bendahan | | 378/57 |
| 2011/0274249 A1 * | 11/2011 | Gray et al. | | 378/87 |
| 2011/0274250 A1 * | 11/2011 | Gray et al. | | 378/87 |
| 2012/0069963 A1 * | 3/2012 | Song et al. | | 378/87 |
| 2012/0307967 A1 * | 12/2012 | Smith | | 378/57 |
| 2014/0185755 A1 * | 7/2014 | Bendahan | | 378/57 |

* cited by examiner

*Primary Examiner* — Thomas R Artman
(74) *Attorney, Agent, or Firm* — Novel IP

(57) ABSTRACT

The present application discloses a system for scanning a shoe for illegal materials. The system includes an X-ray source for projecting a beam of X-rays onto the shoe, a detector array for detecting X-rays transmitted through the shoe and at least one metal detector coil for detecting metals within the shoe. The system produces a radiographic image of the shoe by processing the detected X-rays and data obtained from the at least one metal detector coil. Other embodiments are directed toward other screening technologies, including millimeter wave screening technologies.

12 Claims, 17 Drawing Sheets

X-RAY BASED SYSTEM AND METHODS FOR INSPECTING A PERSON'S SHOES FOR AVIATION SECURITY THREATS

CROSS-REFERENCE TO RELATED APPLICATIONS

The present invention relies on, for priority, U.S. Provisional Patent Application No. 61/262,176, entitled "X-Ray Based System and Methods for Inspecting a Person's Shoes for Aviation Security Threats" and filed on Nov. 18, 2009, which is herein incorporated by reference in its entirety. In addition, the present invention relies on U.S. Provisional Patent Application No. 61/313,772, entitled "Walk-Through People Screening System" and filed on Mar. 14, 2010, which is herein incorporated by reference in its entirety, for priority.

FIELD OF THE INVENTION

The present invention relates generally to the field of radiant energy imaging systems for detecting concealed objects, and more specifically to an X-ray inspection system for inspecting shoes of persons for security threats.

BACKGROUND OF THE INVENTION

At various ports of entry, secure buildings, and other locations, the inspection of people, in addition to luggage and cargo, is becoming mandatory. In addition to cargo vehicles, contraband such as explosives, weapons, narcotics, dangerous chemicals, and nuclear and radioactive materials can also be concealed on a person's body for illegal transportation.

Following a report of an individual attempting to destroy a commercial aircraft in-flight by detonating explosives hidden in his shoes, passengers are required to remove their shoes for separate inspection by X-ray systems. The shoe divestiture process causes great inconvenience and delays at checkpoints. Whole body or shoe metal detectors can detect metallic weapons, but result in large false-alarm rate due to the common use of metallic shoe shanks.

Prior art systems for detecting objects concealed on persons do exist but are not adapted to effectively screen the shoes of passengers. For example, U.S. Pat. No. 5,181,234 (hereinafter, the "'234 patent"), assigned to the assignee of the present invention, and herein incorporated by reference in its entirety, describes "[a] pencil beam of X-rays is scanned over the surface of the body of a person being examined. X-rays that are scattered or reflected from the subject's body are detected by a detector. The signal produced by this scattered X-ray detector in then used to modulate an image display device to produce an image of the subject and any concealed objects carried by the subject. The detector assembly is constructed in a configuration to automatically and uniformly enhance the image edges of low atomic number (low Z) concealed objects to facilitate their detection. A storage means is provided by which previously acquired images can be compared with the present image for analyzing variances in similarities with the present image, and provides means for creating a generic representation of the body being examined while suppressing anatomical features of the subject to minimize invasion of the subject's privacy."

In addition, U.S. Pat. No. 6,094,472 (hereinafter, the "'472 patent"), also assigned to the assignee of the present invention and incorporated herein by reference, describes a method for using an X-ray backscatter imaging system for searching a subject for concealed objects, "comprising the steps of: moving the subject within a passageway, the passageway having an entrance and an exit; initiating operation of at least one X-ray source upon entry of the subject into the passageway; producing a pencil beam of X-rays having a low dose directed toward a scanning area at a plurality of scanning positions within the passageway; scanning the pencil beam of X-rays over the scanning area; tracking said pencil beam of X-rays to each of said plurality of scanning positions, wherein the tracking is substantially coordinated with forward progress of the subject through the passageway; using a plurality of detectors, detecting X-rays that are backscattered from said pencil beam as a result of interacting with the subject when positioned at each scanning position of the plurality of scanning positions; and displaying a digitally represented image of the detected backscattered X-rays."

Other references, including U.S. Pat. Nos. 7,826,589, 7,796,733, 7,110,493, and 6,665,373, which are hereby incorporated herein by reference, and technologies, including millimeter wave technologies, similarly do not teach an improved way of screening an individual's shoes. Therefore, there is a need for a rapid and low false alarm rate inspection system for scanning a person's shoes without the need for the person to remove their shoes.

What is also needed is an integrated whole body, metal and shoe scanner system that can distinguish shoe metal shanks from actual threat items.

BRIEF DESCRIPTION OF THE DRAWINGS

These and other features and advantages of the present invention will be appreciated, as they become better understood by reference to the following detailed description when considered in connection with the accompanying drawings, wherein.

DETAILED DESCRIPTION OF THE INVENTION

Figure 1A:
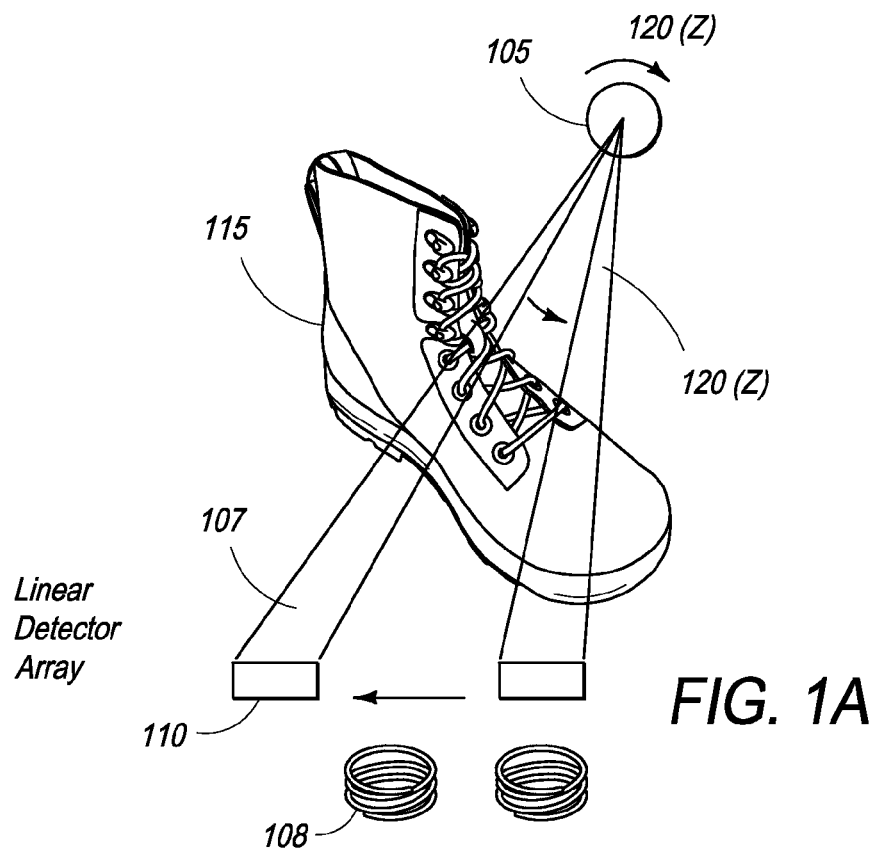
FIG. 1A is an illustration of a transmission X-ray source and detector array as used in one embodiment of the shoe inspection system of the present invention.

The present invention is directed towards X-ray based screening systems to screen a person's shoes for threat items. The present invention, in one embodiment, employs a combination of Rastered Beam Forward Imaging (RBFI) and metal detection for screening a person's shoes and is capable of detecting explosives and threats (metallic and non-metallic) hidden in shoes.

In one embodiment, the present invention is directed towards an X-ray based screening system to screen a person's shoes for contraband, explosives, or other illegal materials, is integrated with a whole body scanner. In one embodiment, the present invention is directed towards a shoe scanning system integrated with a whole body scanner, where the shoe scanner portion advantageously uses the X-ray beam generated by the whole body scanner in conjunction with its own detectors placed under the feet to capture the forward beam.

In one embodiment, the present invention is directed towards a shoe scanning system integrated with a whole body scanner, where the shoe scanner portion has its own dedicated X-ray source and detector arrangement.

In one embodiment, the present invention is directed towards a standalone shoe scanner. In one embodiment, the present invention is directed towards a standalone shoe scanner that uses transmission-based X-ray spectroscopy. In one embodiment, the present invention is directed towards a standalone shoe scanner that uses backscatter detection techniques.

In one embodiment, the present invention is directed towards a standalone shoe scanner that employs a combination of transmission and backscatter detection techniques.

In one embodiment, the present invention is directed towards a shoe scanner that is integrated with a millimeter wave body scanner. U.S. Pat. Nos. 7,385,549, 7,170,442, 7,248,204, 7,194,236, and 6,937,182 are incorporated herein by reference.

In one embodiment, the present invention is directed towards a shoe scanning system integrated with a whole body scanner that employs a single-user interface, thus it does not require additional operators.

In another embodiment, the present invention is directed towards a transmission X-ray based shoe scanner integrated with a whole body scanner wherein the X-ray beam is a rastered forward beam generated from the whole body scanning system.

In yet another embodiment, the present invention is directed towards a backscatter detection based shoe scanner integrated with a whole body scanner.

In yet another embodiment, the present invention is directed towards both a backscatter detection based shoe scanner and a transmission X-ray based shoe scanner integrated with a whole body scanner wherein the transmission X-ray beam is a rastered forward beam generated from the whole body scanning system.

Optionally, all embodiments described above also employ metal detection within the shoe scanner of the present invention.

In one embodiment, the present invention is directed towards a shoe scanning system that can be integrated with a whole body scanner such that it does not increase the total overall footprint of the whole body scanner.

In one embodiment, the shoe threat detection methods of the present invention operate by first receiving, on a computing platform, radiographic images of an object from the shoe scanning system, which comprises at least a radiation source and a corresponding detector array to detect the radiation that is either transmitted through the shoe under inspection or backscattered from the shoe under inspection.

In one embodiment, the shoe scanner portion of the present invention provides for both RBFI-based images as well as metal detection, which in combination allows for a high probability of detection for both explosives and weapons with a low false alarm rate. The system of the present invention is advantageous in that it allows for detection of both metallic and non-metallic weapons, and is capable of detecting explosives regardless of their chemical composition, volatility, and form factor.

In one embodiment, the present invention has low false alarm rates when compared with the use of metal detectors alone as it enables distinguishing metal shoe shanks from actual threats such as weapons, detecting non-metallic weapons, explosives and bombs. In one embodiment, the present invention has improved image quality, higher metal detection sensitivity, and improved left-right asymmetry detection. Thus, anomalies such as left-right shoe anomalies and/or those arising from tampering with the shoes are readily detectable through radiographic images generated with the system of the present invention. In particular, the system of the present invention is able to detect the presence of bulk and sheet explosives placed in one shoe by advantageously using the left-right asymmetry of the shoe images.

In one embodiment, the shoe scanner of the present invention eliminates the need for a person, and in particular, an air travel passenger to remove their shoes at the security checkpoint, thereby increasing checkpoint throughput, enhancing the passenger experience, and improving security. In one embodiment, shoe scanner scan time is 0.5 seconds.

The present invention is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

FIG. 1A is an illustration of an transmission X-ray inspection system for inspecting shoes in accordance with one embodiment of the present invention. FIG. 1A shows a transmission λ-ray source 105 for projecting a pencil beam 107 of X-rays onto a person's shoe 115. The X-ray source 105, in one embodiment, is a single-energy source. However, in an alternate embodiment dual-energy or spectroscopic transmission X-ray source is used. In one embodiment, when the shoe inspection system of the present invention is used as a stand-alone device, the X-ray source energy ranges from 80-140 kV, and particularly if dual energy or spectroscopy is employed. In one embodiment, the shoe inspection system of the present invention employs an X-ray source having an energy in the range of 60 to 120 kV.

Figure 1D:
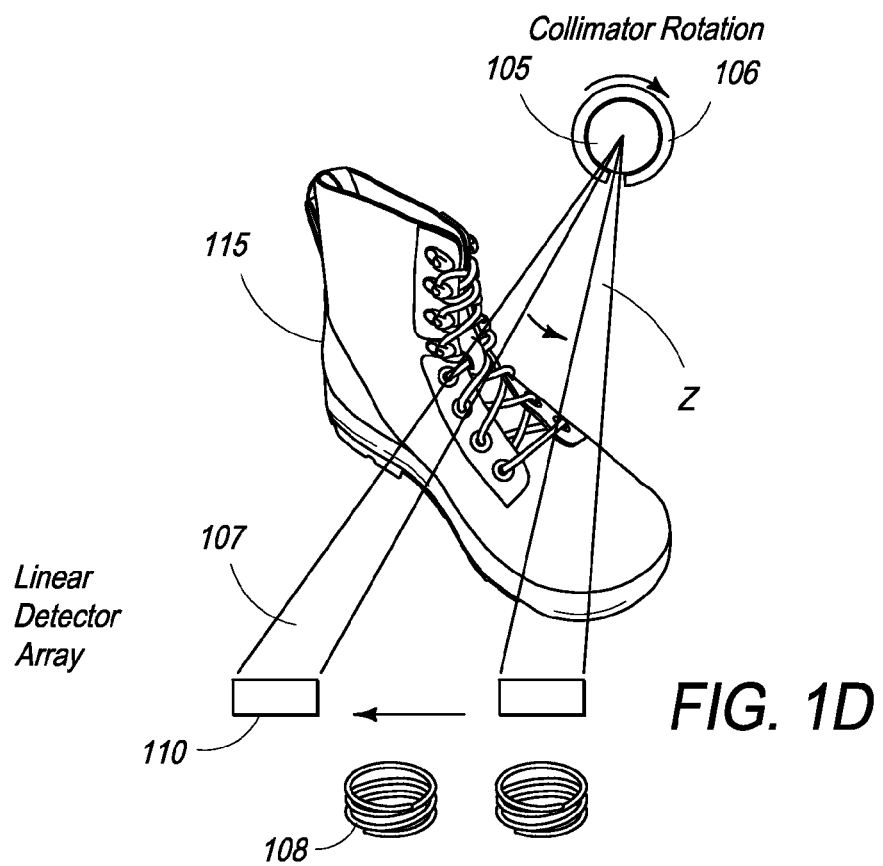
FIG. 1D is an illustration of a transmission X-ray source and detector array as used in one embodiment of the shoe inspection system of the present invention, further showing collimator rotation.

The X-rays transmitted through the shoes 115 are detected by a linear detector array 110 to produce a radiographic image (not shown) of the person's shoe. In one embodiment, segmented and stacked detectors, such as those shown in FIGS. 1A, 1D, and 1E, are employed, and in particular, for dual energy applications. For the system shown in FIG. 1F and described in greater detail below, in one particular embodiment, the detector employed is a flat panel detector, such as those used for digital radiography n medical applications.

As shown in FIG. 1A, the source 105 rotates an angle 120 ("Z") sufficiently large to cover the shoes while a motion synchronized detector array 110, placed underneath the shoe, moves or is translated linearly along an axis which runs along the length of the shoe, in sync with the rotating source to capture unattenuated X-rays emerging from the shoe 115.

In one embodiment, a metal detector comprising one or more metal-detection coils 108 is placed under the shoe to detect metals hidden in the shoe. In one embodiment, the metal detector that is placed within the shoe scanner of the present invention or the Shoe Scanner Metal Detector (SSMD) employs static detection, where the subject is stationary during the measurement. In one embodiment of the SSMD, the metal detector comprises field-generating and field detecting coils that are located on the same panel. In one embodiment, the coil system comprises three field generating coils and six detecting coils on the same panel. The coils are designed such that they are capable of detecting different orientations of metal objects.

One consequence of static detection is that the high pass filtering used to reduce slow signal background drifts cannot be used. To overcome this adverse effect, the background signal is measured continuously while the scanner is unoccupied. Following a shoe scan/measurement, the background signal is subtracted resulting in a net signal. The background signal measurement and subtraction is performed separately for each detection coil.

A second undesired effect of static detection is that at each spatial point of the measurement area, sufficient detection sensitivity for all object orientations is required. This requirement of sufficient 3D sensitivity distribution is an additional challenge for the coil system design. When field generating and detecting coils are on the same plane, the coupling between them can be high, thereby limiting the dynamic range of the detection. While coupling can typically be minimized with proper coil geometry design, geometric constraints from sensitivity distribution requirements make this difficult to achieve in this case. Thus, the coupling is reduced using separate transformers between field generating and detecting coils.

As mentioned above, anomalies such as left-right shoe anomalies and/or those arising from tampering with the shoes are readily detectable through radiographic images generated with the system of the present invention. Separate metal signals are produced from measurement of both the left and right shoes, using separate but identical detecting coils for the left and right shoes. These signals are then used separately to analyze for anomalies compared with signals from different shoe shanks, and for comparing signals of left and right shoes. In order to achieve good sensitivity for all objects regardless of shape or orientation, the coil system in the SSMD of the present invention comprises separate and discrete sets of coils with dominant sensitivities in orthogonal orientations. To ensure that signal differences of left and right detection coils to identical objects are minimized, in one embodiment, field generating coils cover both shoes.

The system produces two signals from each Receiver (RX) coil—a component in-phase with the transmitted (TX) coil and a quadrature component. In one embodiment, signals are produced at a rate of 100 Hz. From these components, it is possible to produce amplitude and phase values for each RX coil. The amplitude is proportional to the metal size and the phase is sensitive to the metal type.

Figure 1B:
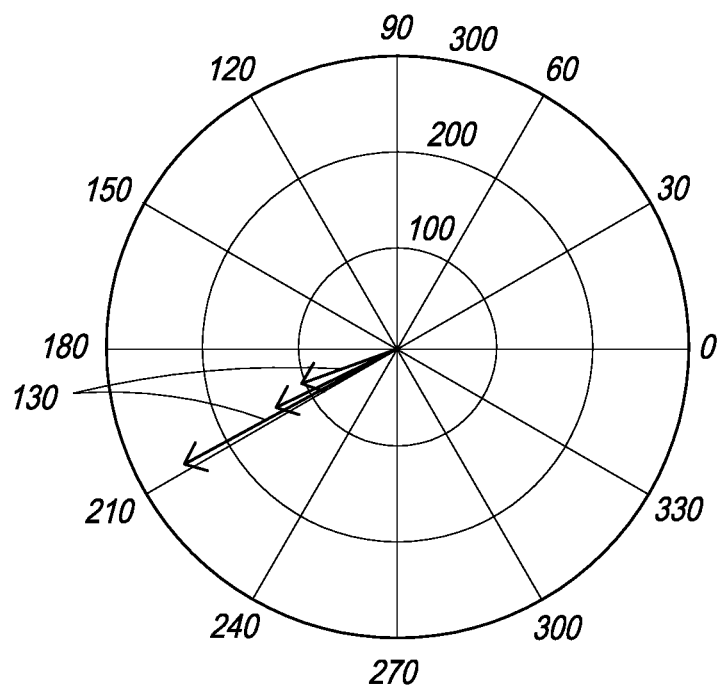
FIG. 1B is a diagram showing sample signals from a selection of different sized shoe shanks.
Figure 1C:
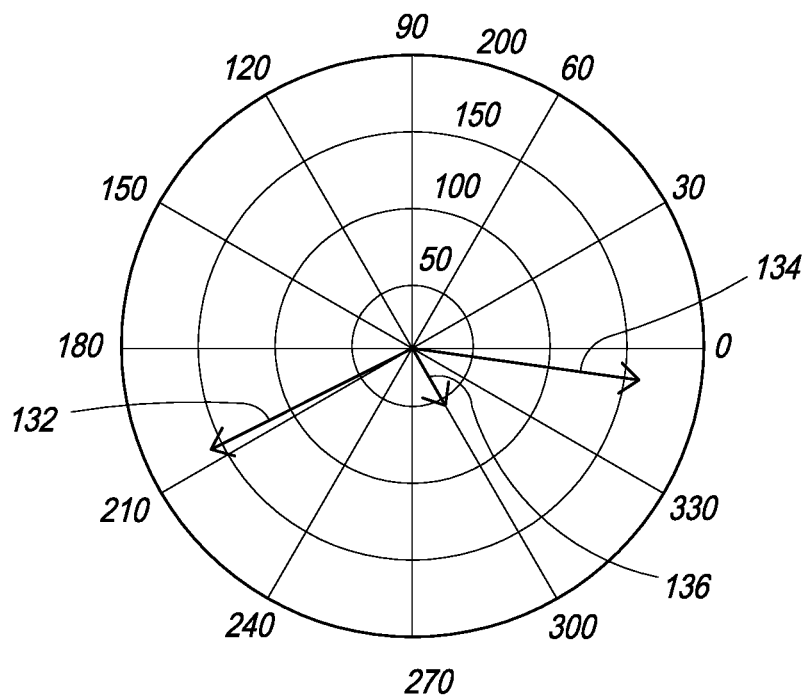
FIG. 1C is a diagram showing signals of objects made from different materials, further illustrating different signal phases.
Figure 1E:
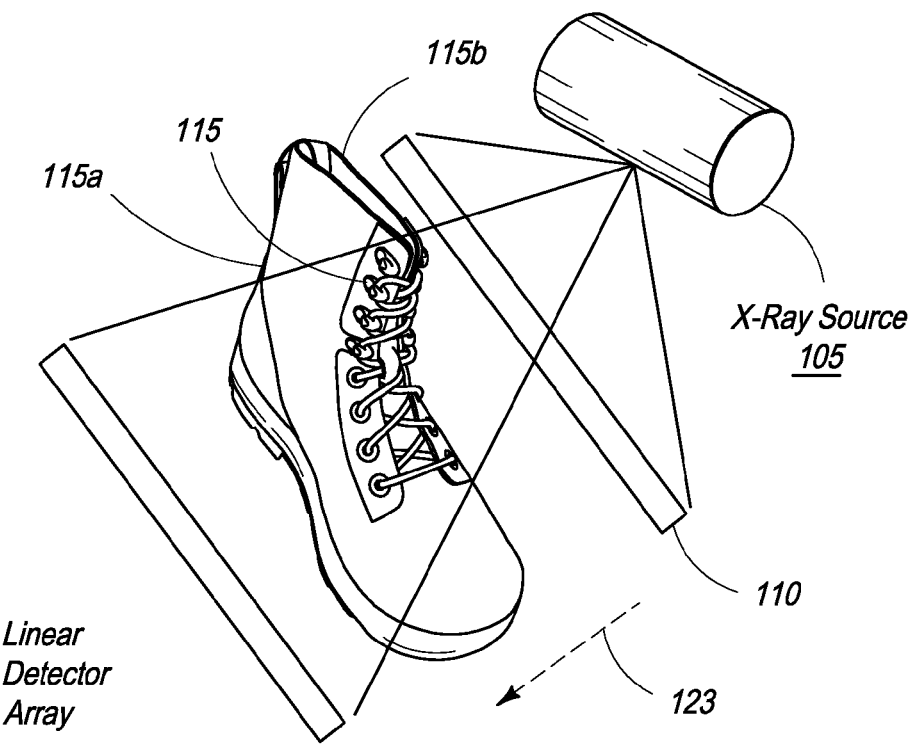
FIG. 1E is an illustration of a transmission X-ray source and detector array as used in one embodiment of the shoe inspection system of the present invention.

FIG. 1B is a diagram showing sample signals from a selection of different sized shoe shanks. The signals 130 indicate that the material used in all the measured shanks is of the same type of metal, since all phases are limited to a narrow sector. The different metal sizes are shown as a variation in vector length. In contrast, as shown in FIG. 1C signals of objects made from different materials show different phases. Signal 132 is a sample signal for steel objects, signal 134 is a sample signal for aluminum objects, and signal 136 is a sample signal for stainless steel objects, all of different phases, indicating that the metal detector will detect threat objects placed in shoes while not alarming on small shoe shanks.

FIG. 1D is another embodiment of the transmission X-ray inspection system for inspecting shoes that employs a source with a rotating collimator 106 instead of a rotating source.

FIG. 1E is another embodiment of the transmission X-ray inspection system for inspecting shoes that employs a linear detector array 110, placed underneath the shoe 115, which moves or is translated linearly along an axis 123 which runs along the width of the shoe, defined by the distance from 115a to 115b, in synchronicity with the X-ray source 105 to capture transmitted X-rays emerging from shoe 115.

Figure 1F:
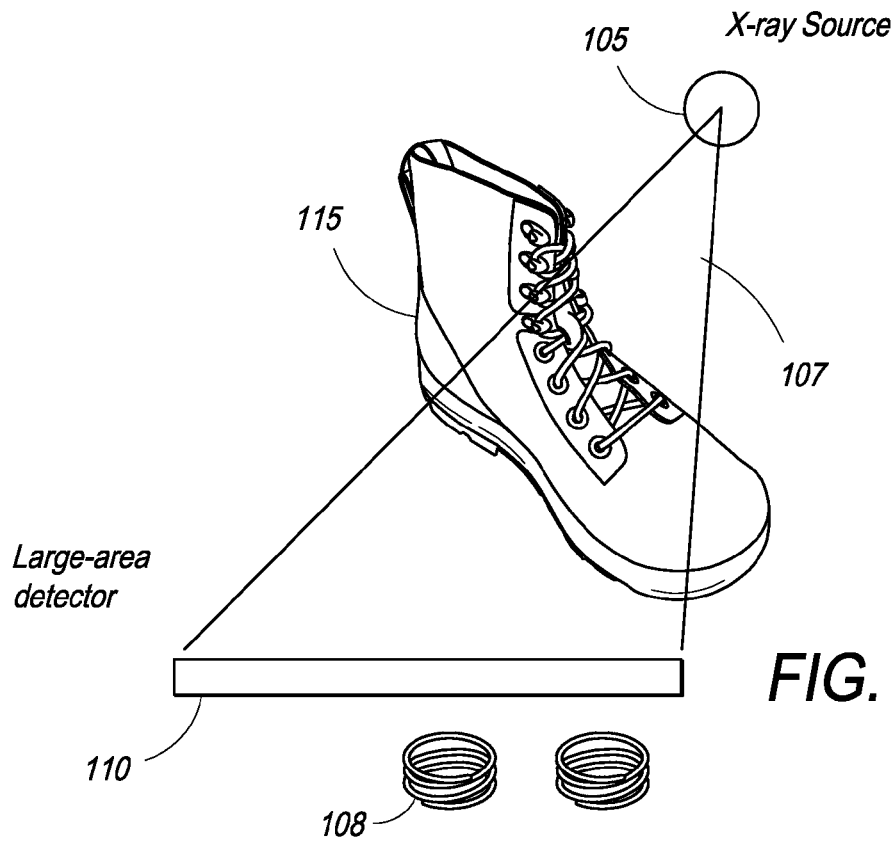
FIG. 1F is an illustration of a transmission X-ray source and detector array as used in one embodiment of the shoe inspection system of the present invention, in which a cone beam of X-rays and a large area detector is employed.

FIG. 1F shows another embodiment of the X-ray shoe inspection system where the source 105 projects a cone beam 107 of X-rays onto shoe 115, and wherein the transmitted X-rays are detected by a large area detector 110. With the use of the cone beam 107, the large area detector 110 is enabled to produce a radiographic image of the shoe 115 in a single scan.

Also shown is a metal detector comprising at least one and preferably one or more metal-detection coils 108.

The embodiments shown in FIGS. 1A, 1D, and 1E employ moving parts with associated complexity, while the embodiment shown in FIG. 1F uses two large stationary large-area detectors with a cone beam, with the trade-off of higher cost. The embodiment shown in FIG. 1F employing at least one large area detector is advantageous in that it allows for higher spatial resolution (on the order of 1 mm), thus enhancing threat detection. As described below, in all other embodiments employing a pencil beam, the spatial resolution is on the order of approximately 5 mm.

Figure 1G:
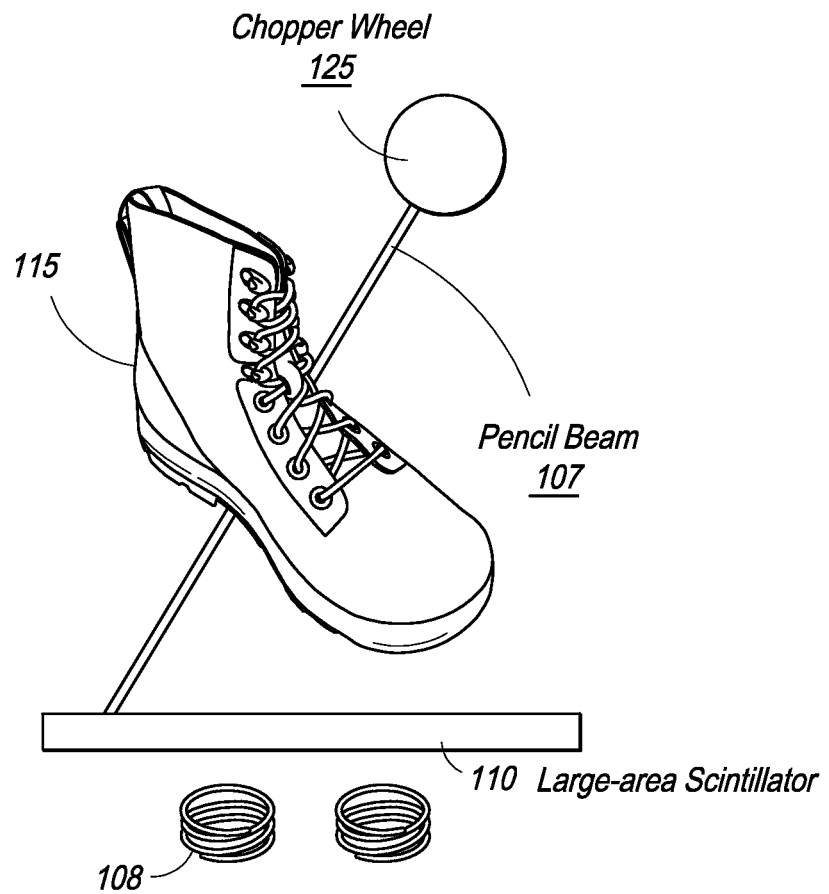
FIG. 1G is an illustration of a transmission X-ray source and detector array as used in one embodiment of the shoe inspection system of the present invention, in which a chopper wheel X-ray source and a large area detector is employed.

FIG. 1G is another embodiment of the transmission X-ray inspection system for inspecting shoes that employs a pencil beam of X-rays with a large area detector. As shown in FIG. 1G, the source 105 projects, via a chopper wheel 125 having at least one aperture, a pencil beam 107 of X-rays, while a large area detector 110 is used to capture transmitted X-rays passing through the shoe 115. In one embodiment, the detector is a substantially wide X-ray area detector for producing a radiographic image of the shoe in a single scan. In one embodiment, the detector is wide enough to cover at least one shoe. In one embodiment, a pair of detectors is used such that a complete image of the shoes can be produced. In one embodiment, the detector is 8" by 20". In one embodiment, the detector is wide enough to cover a pair of shoes and is capable of producing a complete image of the pair of shoes. In one embodiment, the detector is 28" by 20" and covers both shoes. In using one detector, however, there are additional scatter and cost issues.

In one embodiment, one or more metal-detection coils 108 for each shoe are placed under the shoe to detect metals hidden in the shoe.

Figure 1H:
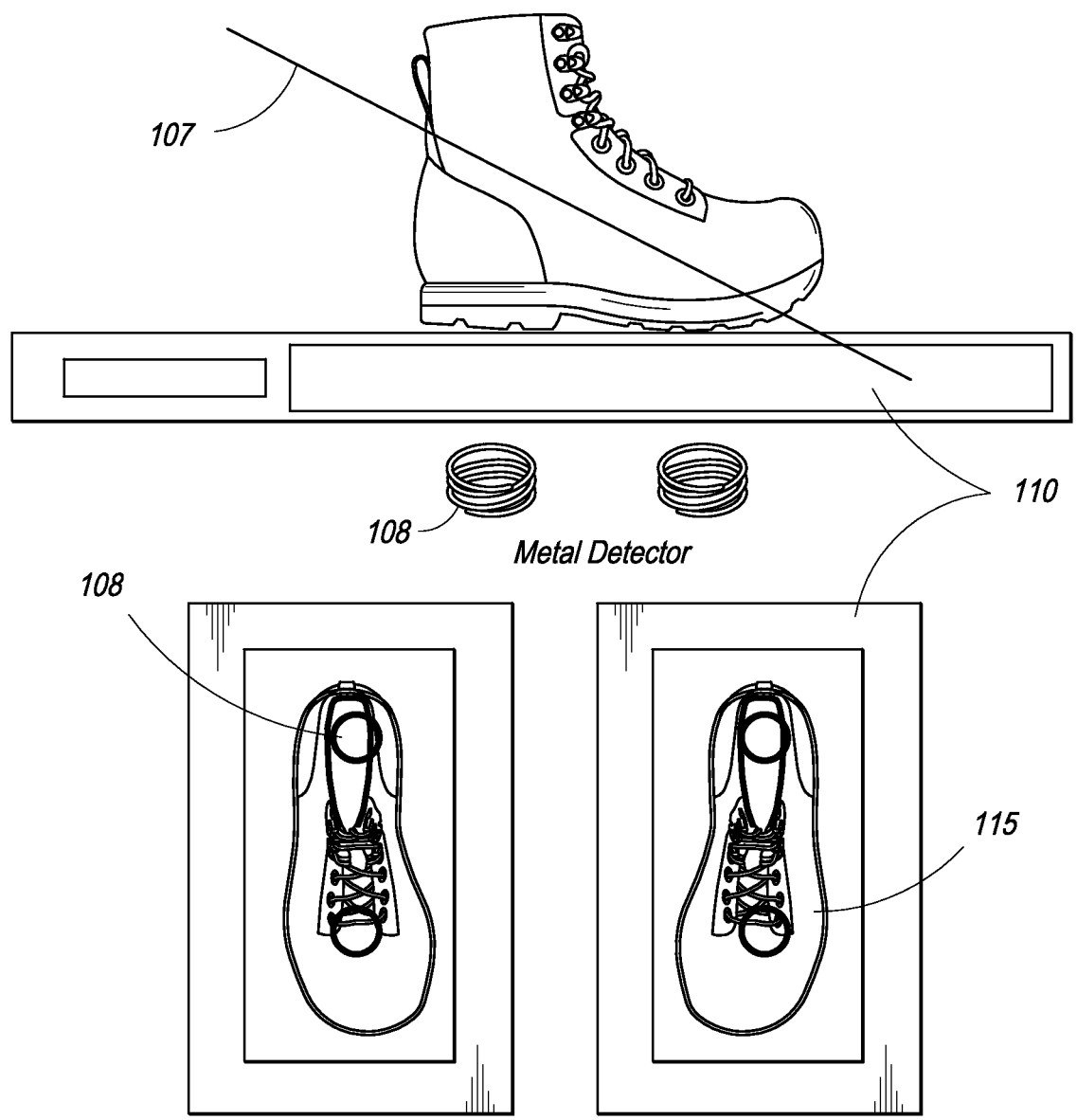
FIG. 1H is top planar view of one exemplary configuration of the shoe inspection system of the present invention.

FIG. 1H is a top planar view of an exemplary configuration of the shoe inspection system of the present invention. FIG. 1H shows metal-detection coils 108 provided for each shoe 115 with the detectors 110 placed under the shoes (X-ray sources not shown). In one embodiment the source is positioned above the person's shoes such that the beam 107 of X-rays is projected onto the shoe 115 from the top. Also, the detectors 110 are placed below the person's shoe 115 to capture the transmitted X-rays. In an alternate embodiment, the source is placed on one side of the shoe 115 while the detectors 110 are positioned on the opposite side.

In another embodiment, the shoe scanner of the present invention is a backscatter inspection system. In one embodiment, the backscatter inspection shoe scanner is a standalone system. In another embodiment, the backscatter inspection shoe scanner is integrated with a whole body scanner, described in greater detail below and shown in FIG. 2A.

Figure 2A:
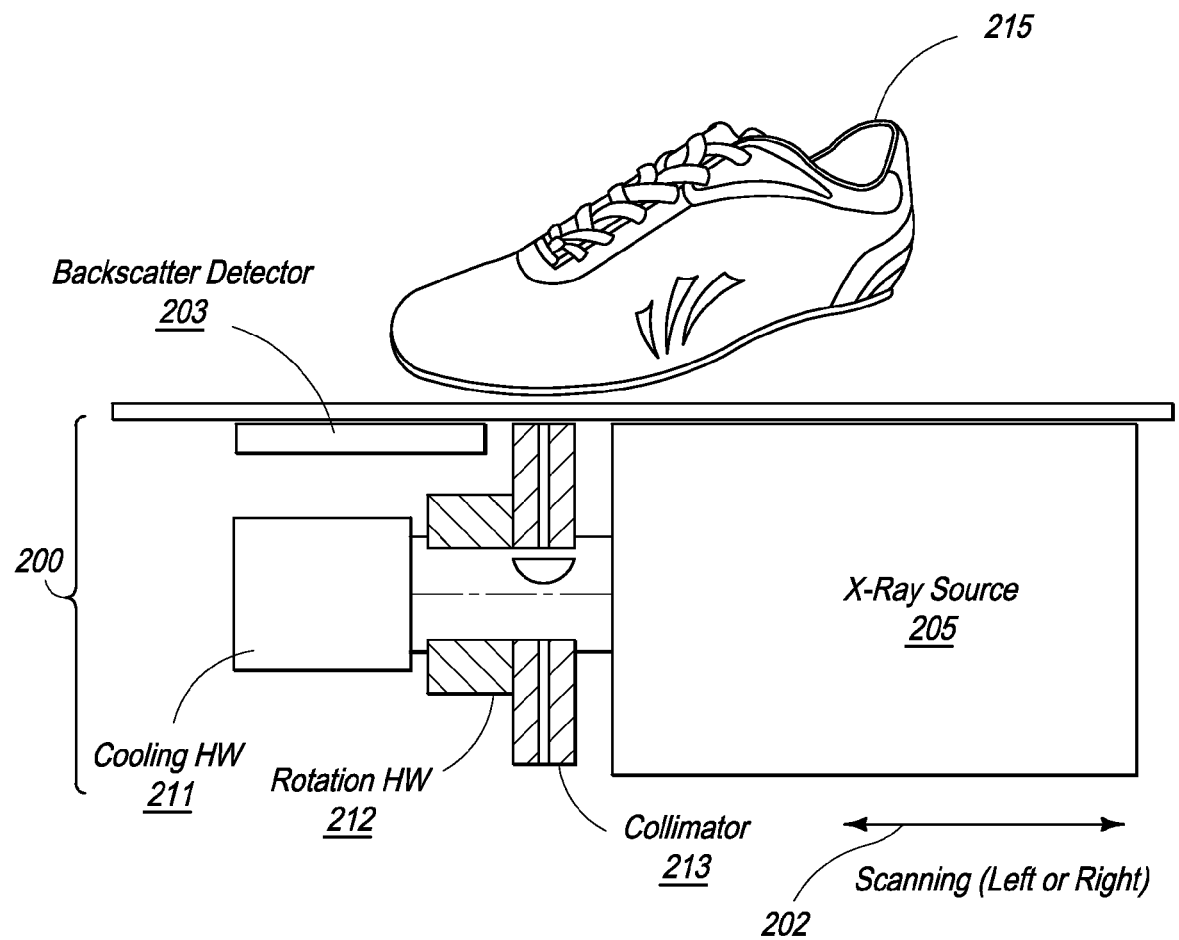
FIG. 2A is an illustration of a backscatter X-ray inspection system for inspecting shoes in accordance with one embodiment of the present invention, in which two backscatter inspection modules are employed.

FIG. 2A is an illustration of a backscatter X-ray inspection system for inspecting shoes in accordance with one embodiment of the present invention, in which one backscatter inspection module is employed. Backscatter inspection system 200 scans a person's shoe 215 from the bottom or from the underside. In one embodiment, the backscatter system comprises X-ray source 205, such as a chopper wheel as described above, a beam scanning mechanism 202 for moving the source from the left to right and vice versa, and X-ray backscatter detectors 203. In one embodiment, the person's shoes are scanned along the length of the shoe. The X-ray detectors 203, in one embodiment, are comprised of photo-multiplier tubes and reside in the area of the backscatter system 200 closest to the shoe. The backscatter inspection module further includes a beam scanning mechanism that comprises cooling hardware 211 for cooling the system components, rotation hardware 212 for translating and/or rotating the X-ray source 203, and a collimator 213 to appropriately collimate the source beam.

In one embodiment, the backscatter inspection shoe scanner of the present invention is capable of producing high resolution images, on the order of less than 1 mm, due to the proximity of the beam to the object under inspection or the shoe. When the beam is closer to the show, there is less beam divergence, and thus greater spatial resolution of the images.

Figure 2B:
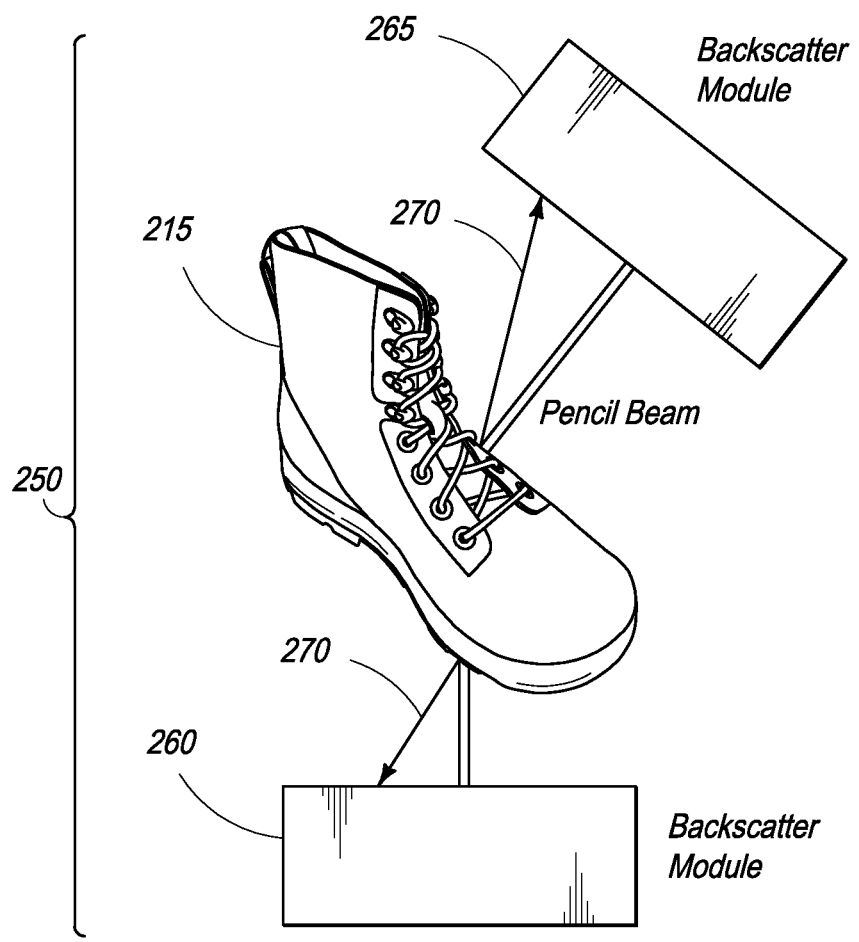
FIG. 2B is an illustration of a backscatter X-ray inspection system for inspecting shoes in accordance with one embodiment of the present invention, in which two backscatter inspection modules are employed.

FIG. 2B is an illustration of a backscatter X-ray inspection system for inspecting shoes in accordance with one embodiment of the present invention, in which two backscatter inspection modules 260, 265 are employed. Backscatter inspection system 250 comprises a first backscatter module 260 that scans a person's shoe 215 from the top and a second backscatter module 265 that is positioned to scan the person's shoe 215 from the bottom or from the underside. In one embodiment, backscatter modules 260, 265 comprise an X-ray source, a beam scanning mechanism, and X-ray detectors, which are described in detail above with respect to FIG. 2A. In one embodiment, the X-ray detectors comprise photo-multiplier tubes that are used to detect backscattered X-rays 270 and are located near a front panel on backscatter modules 260, 265. Optionally, a metal detector comprising one or more metal-detection coils, as described above, is placed under the shoe to detect metals hidden in the shoe.

In another alternate embodiment, a plurality of backscatter modules is employed. Thus, one backscatter module is employed to scan the soles or bottoms of the shoe, another backscatter module is employed to scan the top side of the shoe, yet another backscatter module is employed to scan the right side of the shoe and yet another backscatter module is employed to scan the left side of the shoe. Thus, any number of backscatter modules may be employed in order to scan the entire shoe or shoes on a person.

Figure 3:
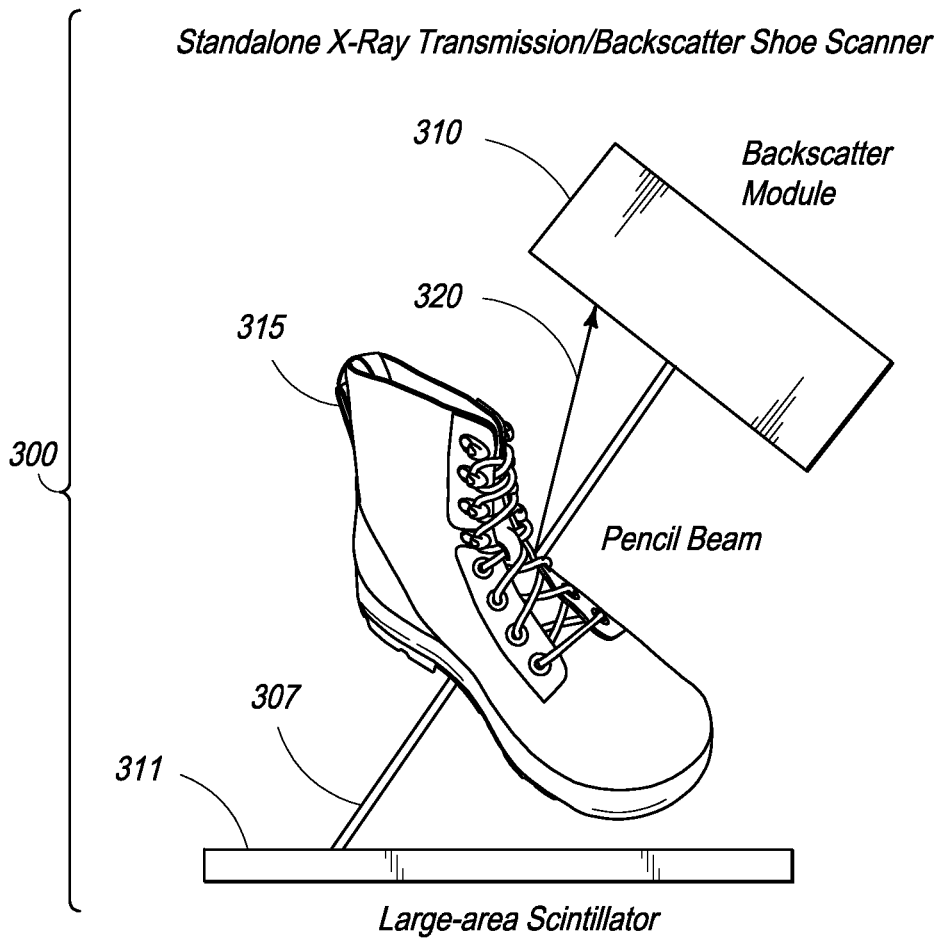
FIG. 3 is a depiction of an integrated transmission and backscatter X-ray inspection system for inspecting shoes in accordance with an embodiment of the present invention.

FIG. 3 is an illustration of an integrated transmission and backscatter X-ray inspection system for inspecting shoes in accordance with an embodiment of the present invention. In one embodiment, system 300 uses a combination of transmission and backscatter radiographic information for improved threat detection. In one embodiment, the transmission images and backscatter images are processed and analyzed separately. In one embodiment, the images are data-fused. X-ray inspection system 300 comprises a backscatter module 310 that projects a pencil beam 307 of X-rays over a person's shoe 315 from the top. A large-area detector 311, for example, but not limited to, a scintillator and with photomultiplier tubes, is positioned on the side opposite to the backscatter module 310 to capture X-rays 309 transmitted through the shoe 315. In one embodiment, the large area detector is a plastic scintillator made of polyvinyl toluene (PVT) that is fabricated from approximately 1" of PVT with a co-planar PMT. In one embodiment, the detector 311 is placed below the shoe 315. The backscatter module 310 comprises an X-ray source, a beam scanning mechanism, and X-ray detectors. In one embodiment, the X-ray detectors comprise photo-multiplier tubes that are used to detect backscattered X-rays 320 and are located near a front panel on backscatter module 310. Optionally, a metal detector comprising one or more metal-detection coils, as described above, is placed under the shoe to detect metals hidden in the shoe.

In one embodiment, the systems shown in FIGS. 1A, 1D, 1E, 1F, 1G, 1H, 2, and 3 are deployed prior to persons going through body metal detectors. In one embodiment, the metal detectors are set such that they do not alarm for metals in shoes thereby reducing the overall rate of false alarms. It should be noted herein that the image of shoes that is obtained using the whole body scanner typically has quite low resolution. Thus, the whole body scanner cannot be used alone to detect threat items contained in shoes. As such, an additional shoe scanner is needed.

Figure 4A:
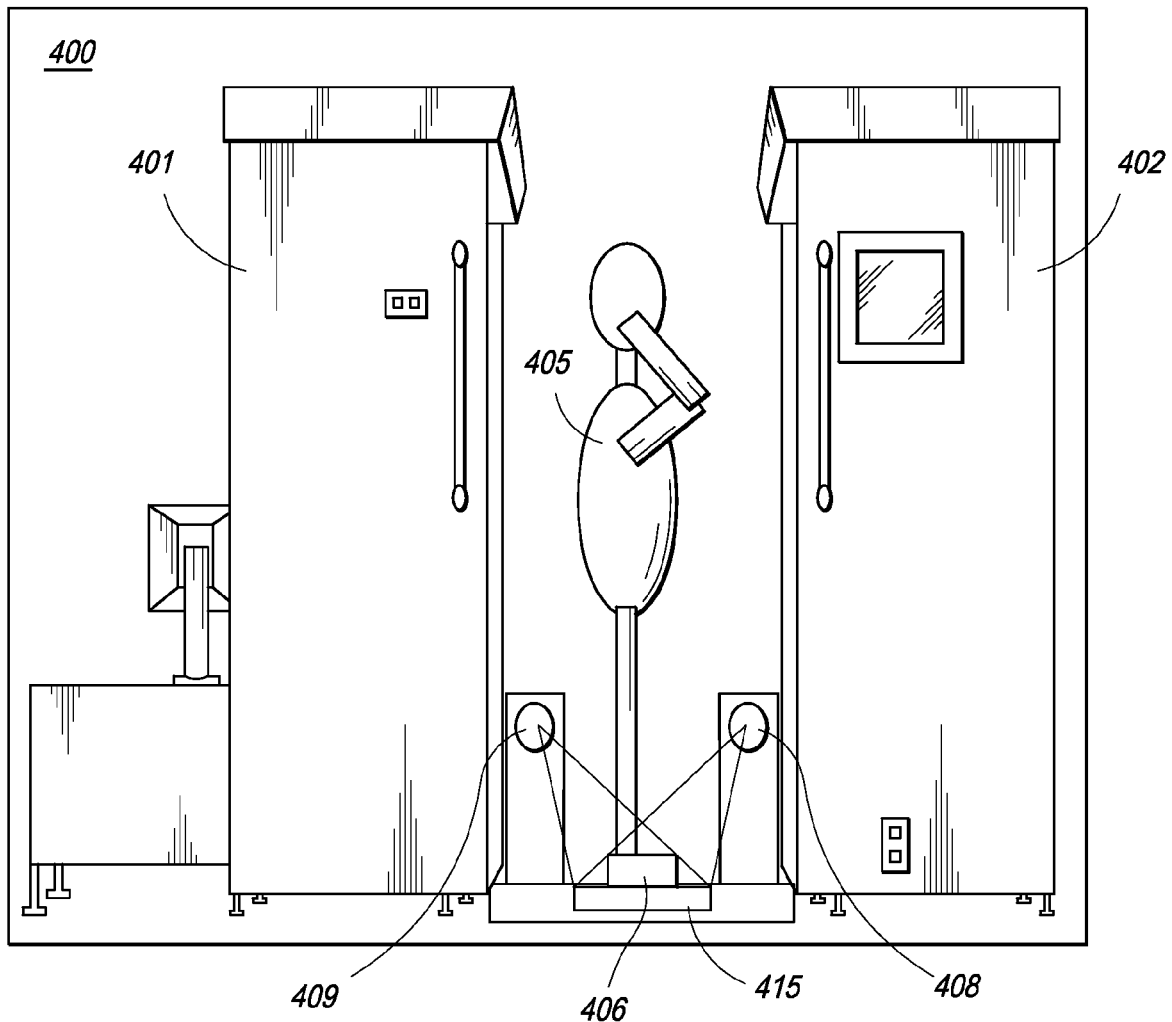
FIG. 4A is an illustration of another embodiment of a whole body scanner integrated with the shoe inspection system of the present invention.

FIG. 4A is an illustration of one embodiment of a whole body scanner integrated with the shoe inspection system of the present invention, in which the shoe inspection system is a separate module having its own source and detector array, housed within the whole body scanner. In one embodiment, the shoe inspection module is a transmission-based X-ray inspection system. In an alternate embodiment, a backscatter inspection shoe scanner module, as described above, is integrated with a whole body scanner.

Figure 4B:
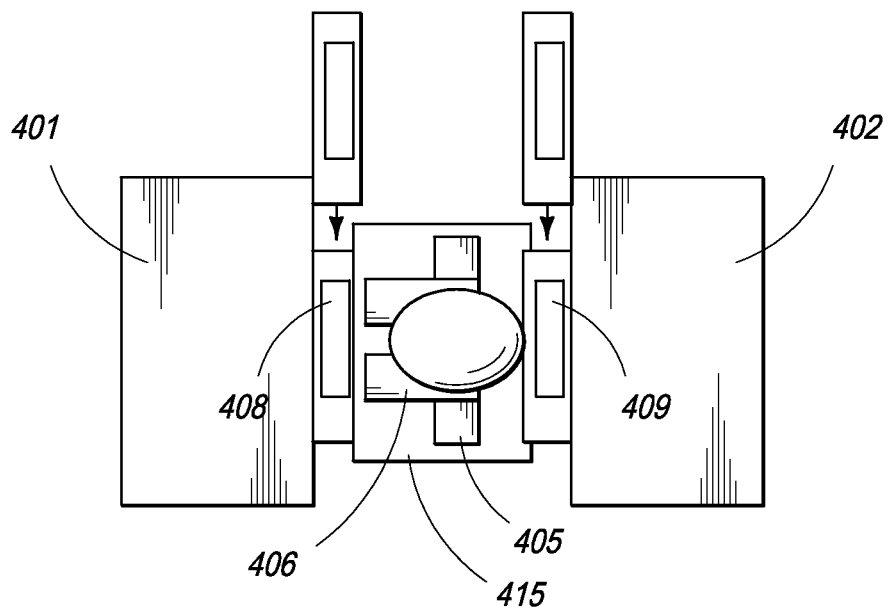
FIG. 4B is a top planar view of the whole body scanner integrated with the shoe inspection system of the present invention, as shown in FIG. 4A.

FIG. 4B is a top planar view of another embodiment of a whole body scanner integrated with the shoe inspection system of the present invention, as shown in FIG. 4A. Referring now to FIGS. 4A and 4B, in one embodiment, the source modules 408, 409 are outside the scanning area when the whole-body system starts scanning person 405. While whole body scanner 401 first scans a first side of person 405 who is located in area 415, source module 408 of the shoe scanner starts to move into position. Thereafter, whole body scanner 402 scans a second side of a person 405. After the second side of the person 405 is scanned, source module 409 of the shoe scanner starts to move into position, while source module 408 scans the person's shoes 406. Once the whole-body scan is complete, source module 408 starts moving back to its original position, while source module 409 scans the person's shoes 406. Once, the scan is completed, person 405 is instructed to leave the area while source module 409 moves back to its original position. It is understood that the described time-staggered motion of components is done to reduce time. In another embodiment, the source modules 408 and 409 could be moved into position after both sides of the body are scanned. In another embodiment, there is only one source module 408 or 409.

Figure 4C:
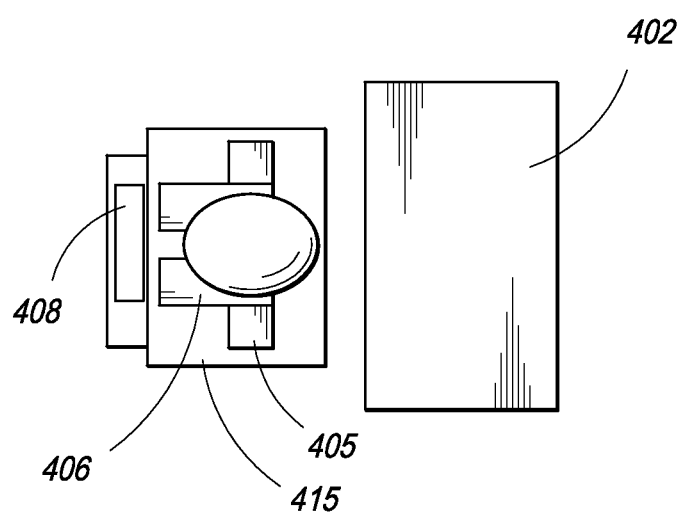
FIG. 4C is a top planar view of a single-sided shoe scanner integrated with a single-sided whole body scanner in accordance with another embodiment of the present invention.

FIG. 4C is a top planar view of the shoe scanner of the present invention integrated with a single-sided whole body scanner 402 in accordance with another embodiment of the present invention. In this particular embodiment, there is only one shoe scanning module 408 placed on the opposite side of the single-sided whole-body scanner 402. Once the whole body scanner 402 completes a scan of person 405, shoe scanner module 408 scans the person's shoes. The person is then instructed to turn around and the process is repeated.

In one embodiment, the platform 415 upon which the person under inspection stands is elevated to approximately 2 inches above ground level. In one embodiment, a platform and rails are employed to prevent tripping and/or falls.

U.S. Pat. No. 5,181,234, assigned to the assignee of the present invention, entitled "X-ray Backscatter Detection System" and issued on Jan. 19, 1993 is herein incorporated by reference in its entirety.

In addition, U.S. patent application Ser. No. 12/887,510, also assigned to the assignee of the present invention, entitled "Security System for Screening People", and filed on Sep. 22, 2010, is herein incorporated by reference in its entirety.

Further, U.S. Pat. No. 7,826,589, also assigned to the assignee of the present invention, entitled "Security System for Screening People", and issued on Nov. 2, 2010, is also herein incorporated by reference in its entirety.

Still further, U.S. Pat. Nos. 7,418,077 and 7,660,388, also assigned to the assignee of the present invention, entitled "Integrated Carry-On Baggage Cart and Passenger Screening Station", and issued on Aug. 26, 2008 and Feb. 9, 2010, respectively, are herein incorporated by reference in their entirety. In addition, U.S. patent application Ser. No. 12/643,021, entitled "Integrated Carry-On Baggage Cart and Passenger Screening Station" and filed on Dec. 21, 2009, also assigned to the assignee of the present invention, is herein incorporated by reference in its entirety.

Figure 5A:
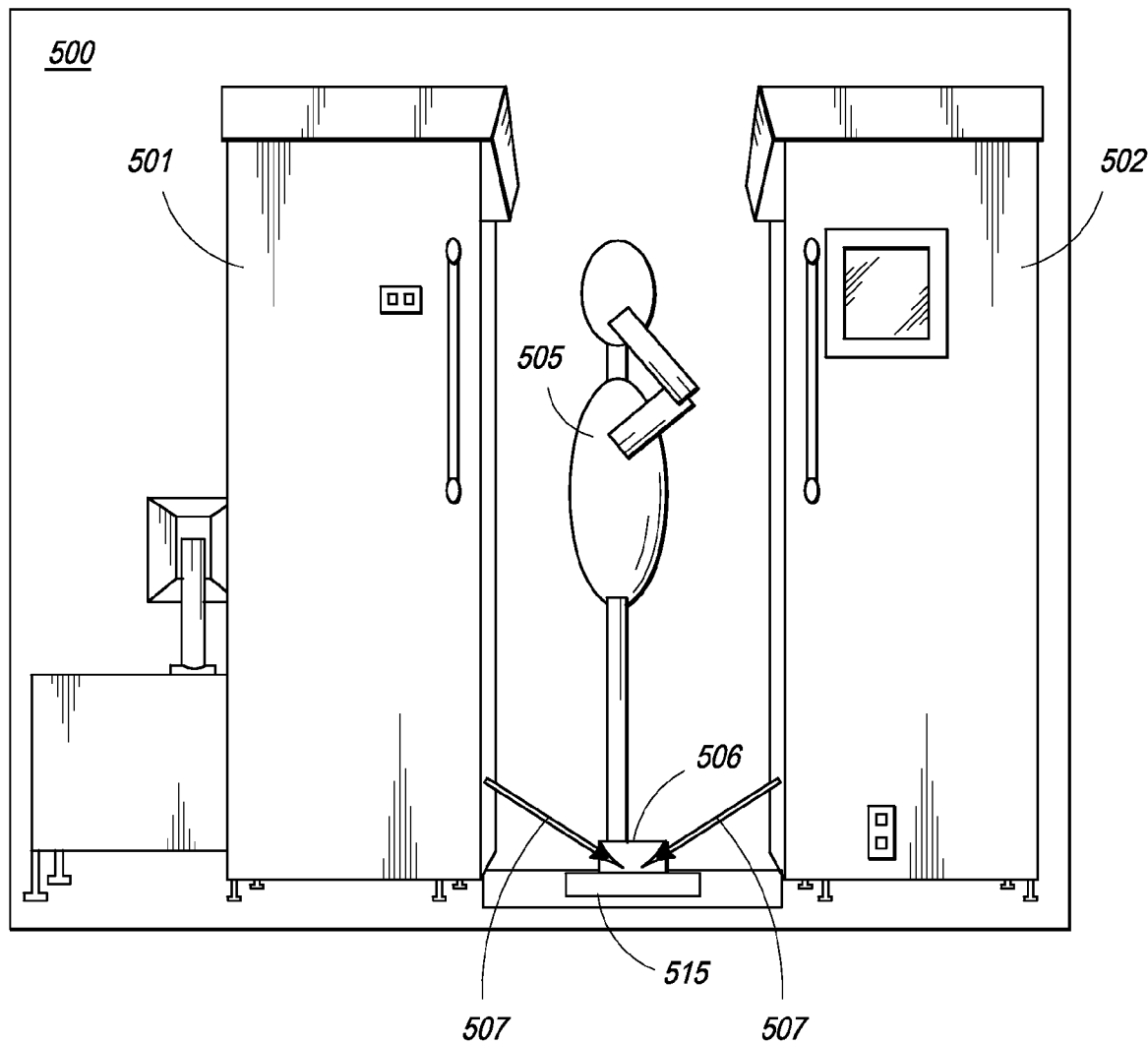
FIG. 5A is an illustration of a whole body scanner integrated with the shoe inspection system of the present invention, in accordance with another embodiment.
Figure 5B:
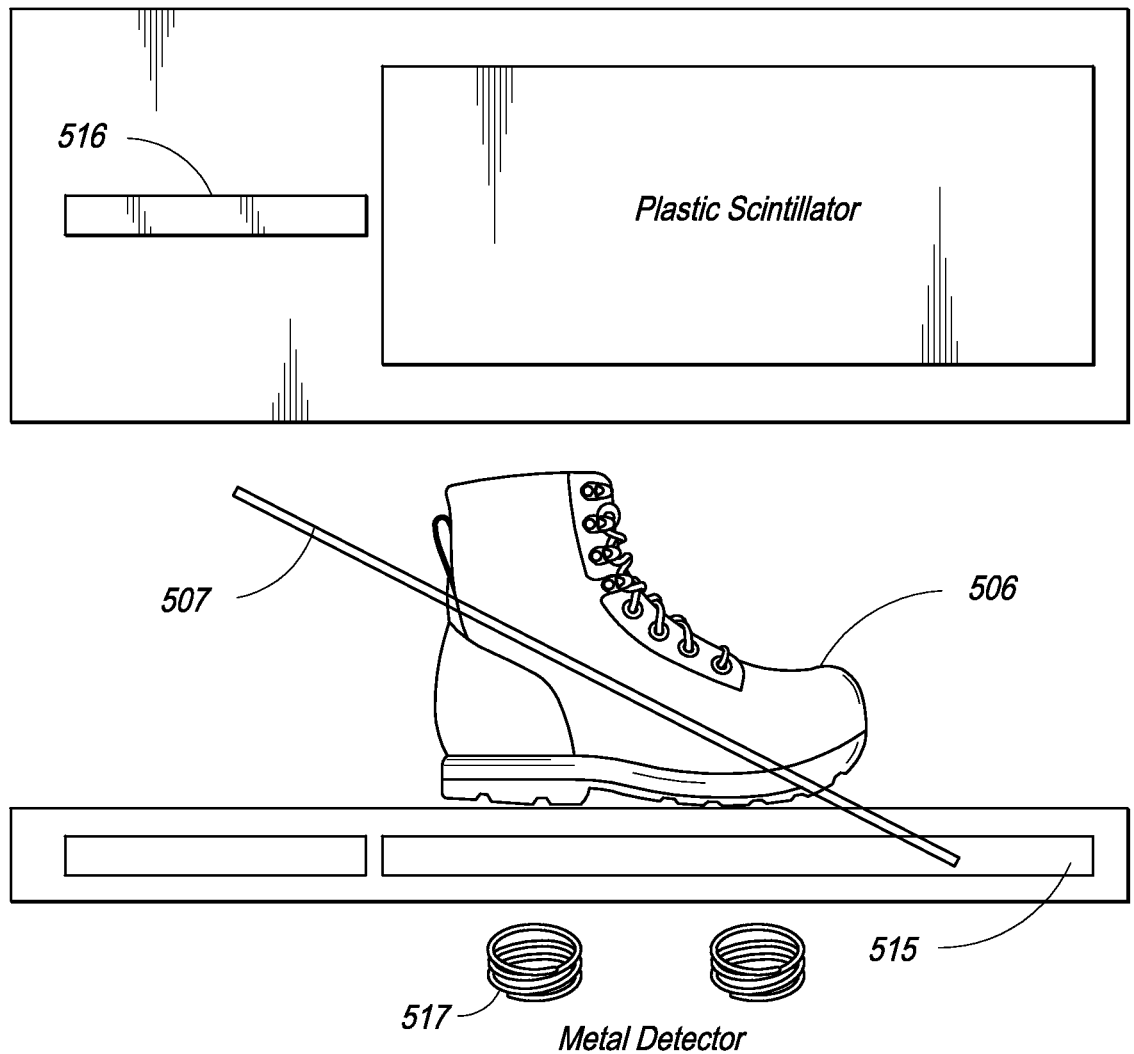
FIG. 5B is an illustration of the detector of one embodiment of the shoe inspection system of the present invention, further equipped with optional metal detecting equipment.

FIG. 5A is a side view of the shoe inspection system of the present invention integrated with a whole body scanner 500 in accordance with another embodiment. In one embodiment, the whole body scanner 500 is a dual-sided system that comprises first scanner booth 501 and second scanner booth 502 that house an X-ray source and at least one backscatter detector for scanning the body of person 505. FIG. 5B is an illustration of one embodiment of the shoe inspection system of the present invention, further equipped with optional metal detectors.

It should be noted herein that while an embodiment of the shoe scanning system of the present invention is described with respect to integration with a dual-sided whole body scanning system, the shoe scanning system of the present invention can also be integrated with a single-sided whole body scanning system. Thus, in one embodiment system 500 is a single-sided scanner where a person is scanned from one side at a time.

Figure 5C:
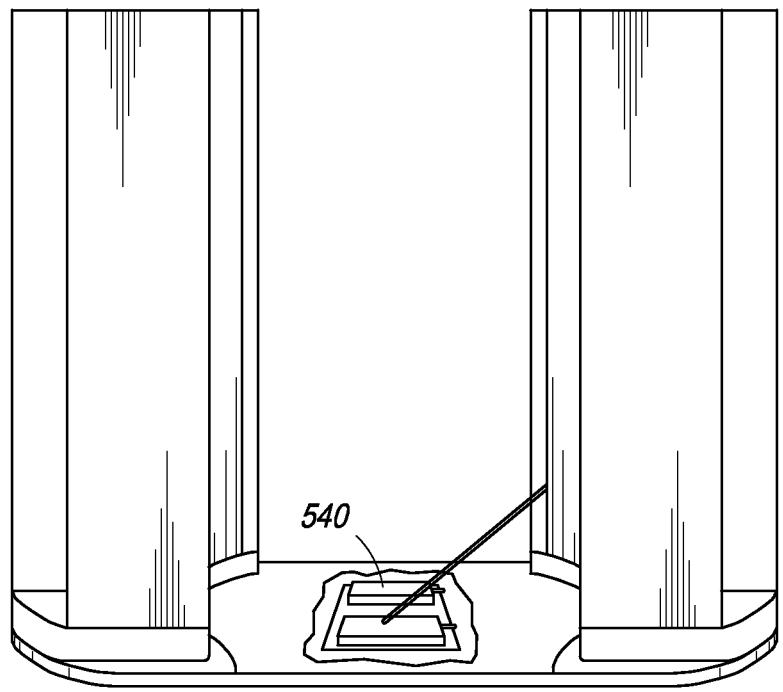
FIG. 5C is an illustration of another embodiment of the shoe inspection system of the present invention.

Referring now to FIGS. 5A and 5B, in one embodiment, detectors 515 are placed underneath the feet (or on the floorboard portion of the whole body scanner, shown in greater detail in FIG. 5C) to capture a forward beam of X-rays 507. In one embodiment, a pencil beam of X-rays 507 generated by the whole-body scanner is projected onto the person's shoe 506. A large area scintillator 515, with photomultiplier tubes 516, is placed under the shoe 506 to detect the transmitted X-ray signals from the scanning pencil beam 507. In one embodiment, the detectors are incorporated into the same electronics architecture as the whole body scanning system and employ common components and communications interfaces.

In an alternate embodiment, a backscatter inspection shoe scanner module, as described above, is integrated with a whole body scanner.

If a backscatter module is employed close to the feet, the distance required from the source to the foot is small so the beam divergence is low, resulting in good spatial resolution (where beam width is the main factor affecting spatial resolution).

In yet another alternate embodiment of the present invention, both forward pencil-beam (transmission-based) X-ray shoe scanning system and backscatter detection capability, as described in detail above, are integrated with a whole body scanner. In one embodiment, a backscatter module is placed under the feet.

In one embodiment, the energy of the beam 507, its intensity and/or scanning time are increased at the foot level to allow for higher penetration through the shoe and shoe metallic areas, also described in greater detail below.

Referring now to FIG. 5B, optionally, a metal detector comprising one or more metal-detection coils 517 is placed under the shoe to detect metals hidden in the shoe. Information from the metal detection coils 517, for each shoe, is integrated with X-ray radiographic information for improved threat detection, as described in further detail below.

FIG. 5C is a side view illustration of the shoe inspection system of the present invention integrated with a whole body scanner 500, further showing a cut-away view of the shoe inspection system 540. In one embodiment, the shoe inspection system 540 components are housed in a slim enclosure and placed inside the floor structure of the whole body scanner with a sloped ramp for easy and safe access. In one embodiment, the detector is a plastic scintillator contained within the floor structure that the passenger stands upon. In one embodiment, the floor-located detector is configured to detect the transmitted forward X-ray beam, rather than the backscattered X-rays.

In operation, the metal detector portion of the shoe scanning system of the present invention first performs a half-second measurement. Second, a first side of the body, including the feet with shoes, is scanned. Immediately after, a second side of the body is scanned. The shoe ATR, described in detail below, begins after the first side of the body is scanned and is completed less than one second after the second side of the body is scanned, simultaneously with the whole body scan ATR.

In one embodiment, the horizontal and/or the vertical scanning speed, beam resolution, beam current and/or voltage of the X-ray source of the whole body scanner are optionally adjusted to allow for improved image quality of the shoes. In a further embodiment the shoes are scanned at a second energy to allow obtaining dual-energy information. In one embodiment, the second energy is a higher energy than the first energy.

In one embodiment, image quality is improved using at least one of enhanced resolution, reduced scatter and reduced noise. In one embodiment, improved resolution is achieved with using an X-ray beam on the order of 4.7 mm. In one embodiment, improved resolution is achieved by adjusting the focal spot size of the X-ray tube, which, in one embodiment is 1.4 mm.

In one embodiment, noise reduction is achieved by reducing the beam aperture size and lowering the beam intensity. In one embodiment, the vertical scanning speed is reduced in the foot area by a factor of four, resulting in a signal increase by a factor of two.

Shoe detectors are typically large area detectors that cover that cover the complete projection of the feet from both sides. In addition to detecting the forward pencil-beam, in one embodiment, a significant scatter from the feet and shoes is measured in the detector array. The scatter increases the observed forward signal, thereby reducing the image contrast. The scatter-to-primary beam ratio increases with attenuation, therefore, pixel with higher attenuation are most affected.

Figure 6A:
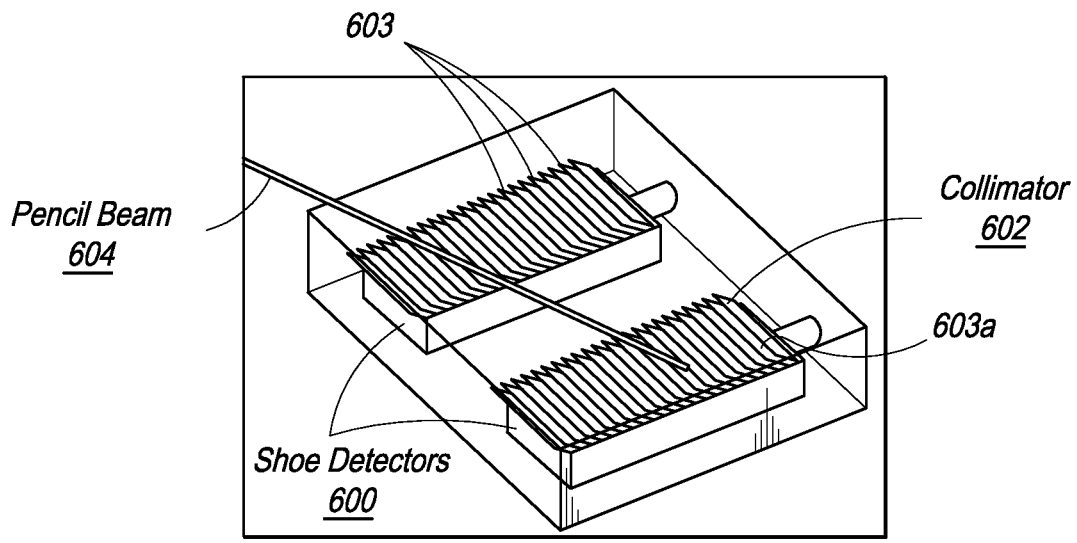
FIG. 6A is an illustration of a detector array including a single-sided collimator, used to achieve scatter reduction in radiographic images.
Figure 6B:
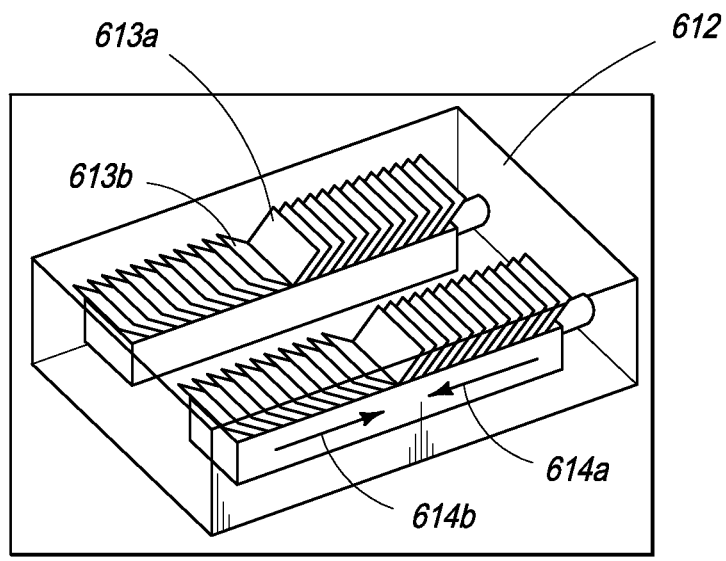
FIG. 6B is an illustration of a detector array including a dual-sided collimator, used to achieve scatter reduction in radiographic images.

In one embodiment, scatter reduction in radiographic images is achieved by using appropriate collimation, as shown in FIGS. 6A and 6B. As shown in FIG. 6A, each shoe detector 600 includes a single-sided collimator 602 comprised of collimator vanes 603. Pencil beam 604 impinges on the sides 603*a* of collimator vanes 603, thereby attenuating it. In one embodiment, due to the low energy of the beam, which is on the order of less than 70 keV, a collimator comprised of collimator vanes having a thickness of less than 1 mm and having a length of less than 20 mm, with a collimator vane spacing on the order of 25 mm is employed. In one embodiment, to prevent shadows, the collimator vanes 603 are parallel to the beam at every position as shown in FIG. 6A.

In using the single-sided collimator shown FIG. 6A, the system is not able to produce images from the other side, since the collimator will block the beam from this angle and it also requires careful alignment and intensity calibration to avoid shadows. Thus, in one embodiment, the collimator is rotated to face the inspection side. In another embodiment, the collimator is a dual-sided collimator 612, comprised of collimator vanes 613*a*, 613*b* as shown in FIG. 6B, where a first half 613*a* of the collimator vanes faces a first direction 614*a* and a second half 613*b* of the collimator vanes 613 faces a second direction 614*b*. This approach allows for producing the best image quality from the side with the highest forward signal.

In one embodiment, collimator vanes 603 are fabricated from non-conducting materials to avoid interference with the metal detector. In one embodiment, the collimator vanes are comprised of a tungsten powder mixed with epoxy and cast in plates.

Figure 7:
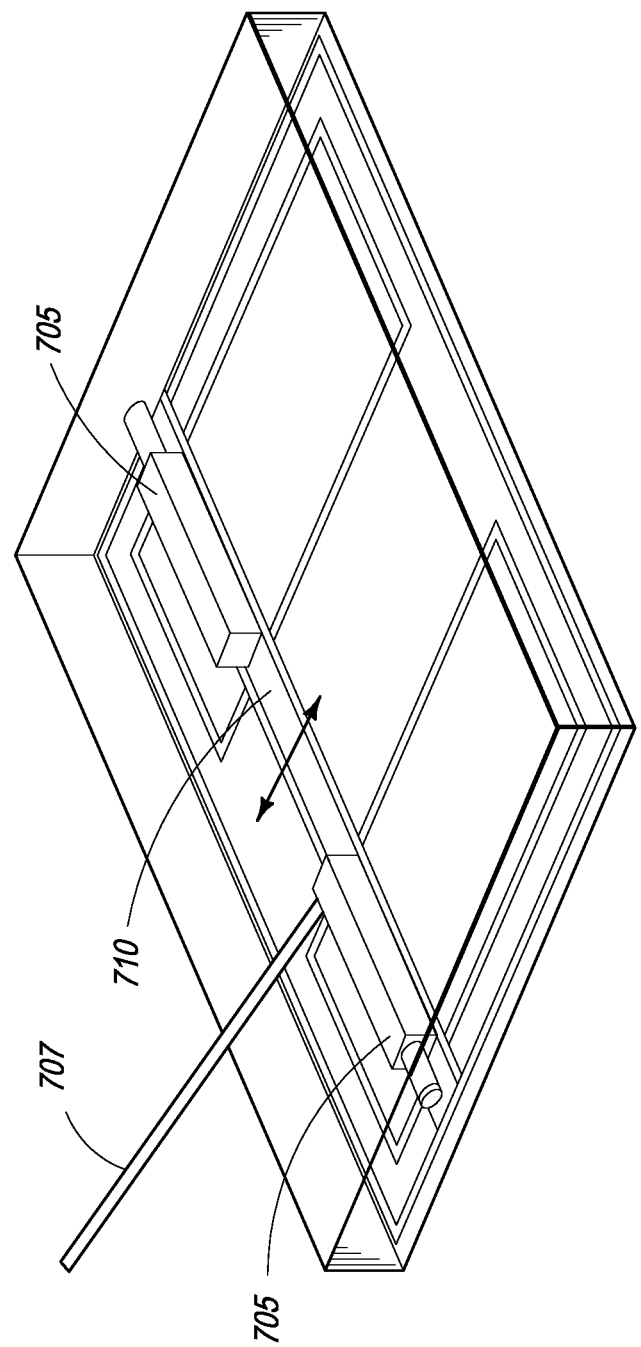
FIG. 7 is an illustration of smaller, movable detectors that are employed to achieve scatter reduction.

In another embodiment, scatter reduction is achieved by reducing the size of the detector. Since the beam moves, the detectors would have to move accordingly to intersect the beam. As shown in FIG. 7, in this approach, two small detectors 705—one under each foot—are employed and placed on a moving mechanism, whereby in one embodiment, the detectors are moved along a width 710, that corresponds to the width of the shoe. In one embodiment, the detectors follow the vertical motion of the beam 707. In one embodiment, the detectors 705 are plastic scintillators having the following dimensions: 8"×18" and a thickness of 1.5". In another embodiment, the detectors are plastic scintillators having the following dimensions: 8" along the width of the foot, 1.5" along the length of the foot and a thickness of 1.5". Since the pencil beam moves, it is necessary to move the detector such that the ebam traversing through the foot is captured by the detector at all times.

In reducing the size of the detectors by a factor of 12, it is possible to substantially reduce the scatter, particularly in areas with high attenuation. In addition, the smaller detector size enables the use of scintillators with higher density and a higher atomic number, such as NaI(Tl), CsI(Tl), BGO, LaBr$_3$, where NaI(Tl) provides the lowest cost of all inorganic scintillators, and thus, is more cost effective. Due to higher efficiency, the detectors can be made smaller, thus reducing scatter even further, and finally, reducing the height of the shoe scanner.

In yet another embodiment, scatter reduction is achieved by use of scatter subtraction algorithms. Algorithms are often used in radiography and computed tomography to correct for scatter effects, which are typically observed in images using large area detectors. In one embodiment, scatter is evaluated as a function of position of various shoes/feet, by shielding a substantial portion of the detector. The shielded portion of the detector will yield transmission results only, while the unshielded detector will yield both transmission and scatter results. The uncovered region is moved to different locations to map the scatter field, which is determined by subtracting the signal with the detector shielding (transmission only) from the unshielded detector (transmission plus scatter). The resultant scatter and transmission maps are employed to determine the scatter-subtraction function.

In another embodiment, increasing the distance between the shoes and the detectors ("air gap") will reduce scatter; however, this adds to the height of the platform and would thereby extend the access ramps needed.

Figure 8:
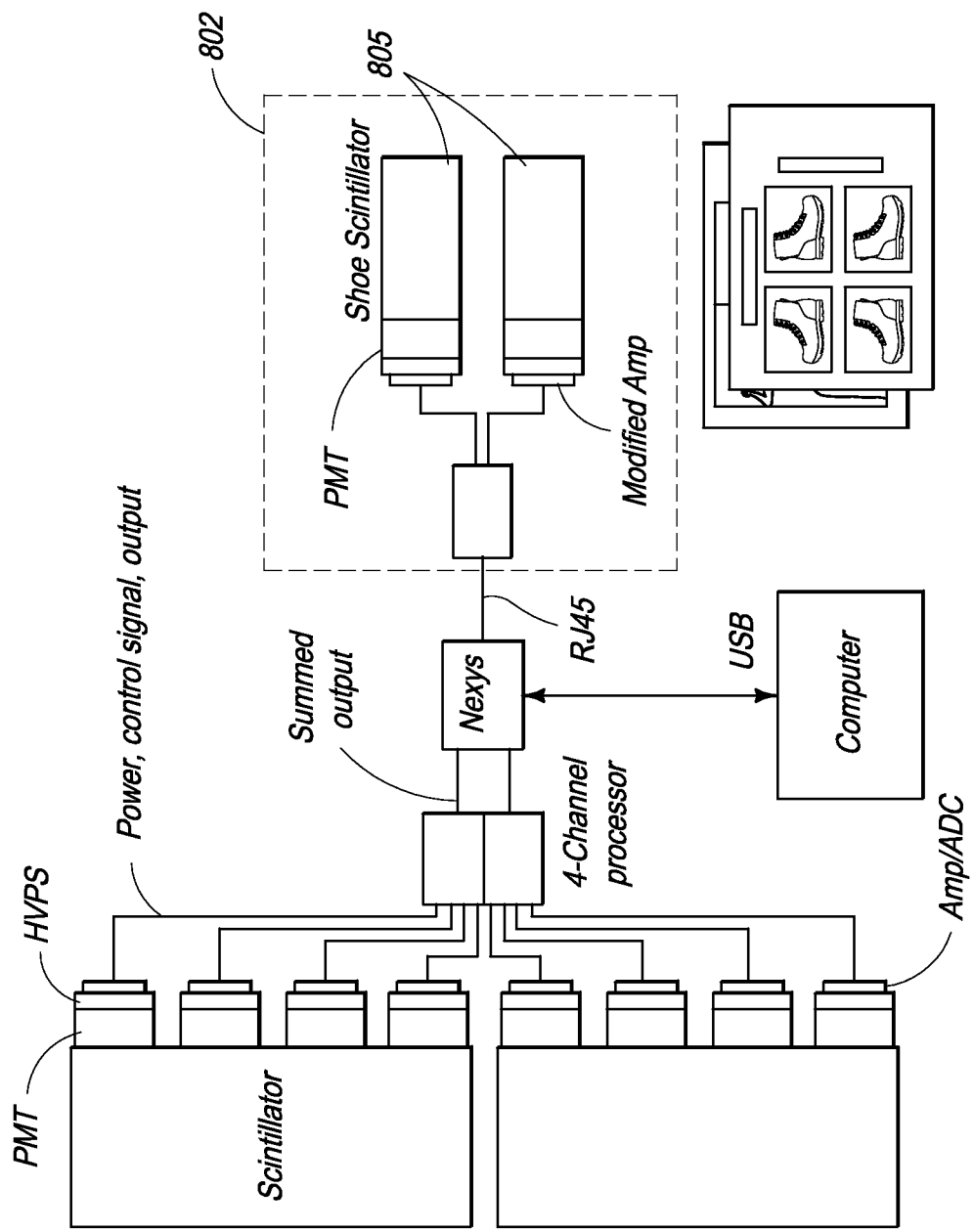
FIG. 8 is a diagram showing the whole body scanner data acquisition system, modified to accommodate for the shoe scanning system data acquisition module.

In one embodiment, both the whole body scanner and integrated shoe scanner use the same data acquisition system. As shown in FIG. 8, the whole body scanner data acquisition system 800 is modified to accommodate for the integrated shoe scanning system data acquisition module 802 by employing two additional detector cards 805 that are electrically connected to the two photomultiplier tubes (PMT) 810 of the shoe-scanner.

Two real-time ports allow for the addition of the shoe scanner acquisition board to the existing system. In one embodiment, signals from the shoe scanner are collected concurrently with the whole body backscatter signals and transferred to a computing system 830. Once data is available it is processed into images which are displayed by the computing system.

One of ordinary skill in the art would appreciate that the data acquisition and image processing features described above in the present application can operate on any computing platform including, but not limited to: a laptop or tablet computer; personal computer; personal data assistant; cell phone; server; embedded processor; main-frame, DSP chip or specialized imaging device. Additionally, the programmatic code can be compiled (either pre-compiled or compiled "just-in-time") into a single application executing on a single computer, or distributed among several different computers operating locally or remotely to each other. It should further be appreciated that all of the method steps disclosed herein, including any and all processing or analytical functions, are implemented in such programmatic code stored in a memory and executed on by at least one processor in the computing platform.

In one embodiment, the software for the shoe scanner of the present invention is developed on a Windows platform. In one embodiment, the software includes a user interface for the operator to control and view system output. Further, buttons are provided on the user interface for starting a scan sequence and viewing results of the scan sequence. In addition, the user interface is designed to provide information regarding the health of the system and subsystems, and the scan states. In one embodiment, the user interface supports different user access levels, whereby a supervisor is granted credentials to access field data and history reports. In addition, the interface provides established standard widgets for a simple development cycle.

In one embodiment, the software for the shoe scanner of the present invention also controls the scan sequence. Thus, beam control, synchronization of master and slave detectors, and parameter switching in the shoe scanner mode is controlled by software. In one embodiment, the system is capable of toggling each detection capability on and off.

In one embodiment, the scan software communicates with scan hardware via a server where raw images are stored.

In one embodiment, the database stores information regarding scans and images. Information on field data such as operator log-in times, operator performance, event logs, and images are available in the database.

In one embodiment, the different software tasks described above communicate with each other using standard socket connections and using a communications library.

In one embodiment, the image processing and detection algorithms are performed within the software component of the shoe scanning system of the present invention, where stored raw images are accessed and processed. Once the image is processed, the results are returned to the user interface for display.

In one embodiment, detection algorithms of the present invention employ data fusion between radiographic and metal-detector images to provide an automated detection (threat/clear decision) or screener-assist indications.

In one embodiment, the radiographic images are presented to an operator on a display, either on location or remotely, for analysis and/or are used to produce automated alarms and/or offer indications to the operator towards areas of concerns. In one embodiment, image information from the whole body scanner is displayed on a first screen or display window. In another embodiment, image information from the integrated shoe scanner, such as a metal signal from the metal detector coils, is shown on a second screen or display window.

In the dual-energy or spectroscopic approaches, the image is processed to show only metal objects or to show only low-atomic number materials. This can be done by toggling the images or having separate windows. This allows for the removal of some image clutter including, but not limited to, a person's bones when analyzing for the presence of anomalies, such as metal.

In one embodiment, and as described below, detection algorithms are based on both automatic threat recognition (ATR) and image inspection by an operator. In one embodiment, the detection algorithms are based entirely on ATR. In an automated approach, the system searches for anomalies that may indicate tampering with the shoes, such as, but not limited to high density areas that may be indicative of explosives, wires, detonators, asymmetries between the shoes and total shoe weight obtained from the transmission images. As described above, metallic threats concealed within one of the shoes can be detected via asymmetry. In addition, in one embodiment, explosives placed within the shoe, both bulk and sheet can be automatically detected by comparing the average attenuation of the shoes.

Metal asymmetry can be also be "detected" when identical shoes are not placed symmetrically from the system's center line, thus causing a false alarm. To counter this false alarm, the shoe position is automatically determined from the images obtained and the metal signal amplitude is adjusted accordingly. When a metal asymmetry is not identified, a metal threat can be detected by analyzing the amplitude and phase of the metal signals for every coil, as described above.

With the improvement in image quality, it is possible to determine the position of metal threats identified by highly attenuating objects in the resultant images, resulting in a reduction of metal detection false alarm rates. If these objects are not seen in the expected position of the shoe shanks, the system will alarm. In some cases, high-density objects will alarm based on shape.

In one embodiment, the system of the present invention houses a library of conventional human anatomy (in particular, the foot) and shoe construction such that the information can be leveraged to determine the presence of anomalies in footwear worn by passengers without using asymmetry detection. It should be noted that feet, hands, and the head are regions of the human anatomy that are least affected by variance in body mass index. Therefore, the attenuation profile of the images through the foot is expected to correlate to the size of the foot. An attenuation model of the shoe and feet is thus generated to collect data for a range of small to large feet with a variety of shoes. Subsequently, a distribution of attenuations is created as a function of foot size. The shoe scanner of the present invention is capable of providing sufficient information in the image to perform at least one of the following: measure the size of the foot under inspection; measure properties of the footwear worn; and/or determine the attenuation profile along the length and across the width of the foot.

By measuring the length and the width of the foot, it is possible to fit the expected attenuation profile generated above to the measured attenuation profile to determine if the measured attenuation through the foot and shoe is consistent with concealed explosive material and whether extra attenuating material is present. In one embodiment, the foot/shoe size is determined automatically by analyzing the image. In one embodiment, multiple measurements are taken along the length of the foot, across the width of the foot, as well as of the foot as a whole to determine whether additional attenuating material has been concealed within the shoe. This procedure is analogous to weighing the shoe with the foot inside. In addition, in using the detection algorithms of the present invention, it is also possible to analyze the attenuation profile for unexpected changes in the profile shape which may be characteristic of concealed explosives.

Other image processing features are also employed and include a first rough segmentation step and at least one of creating a segmented area, determining a mean value, determining the standard deviation, and creating a histogram of values. The quality of the feature chosen is correlated with the quality of the image and the algorithm that is used.

Figure 9:
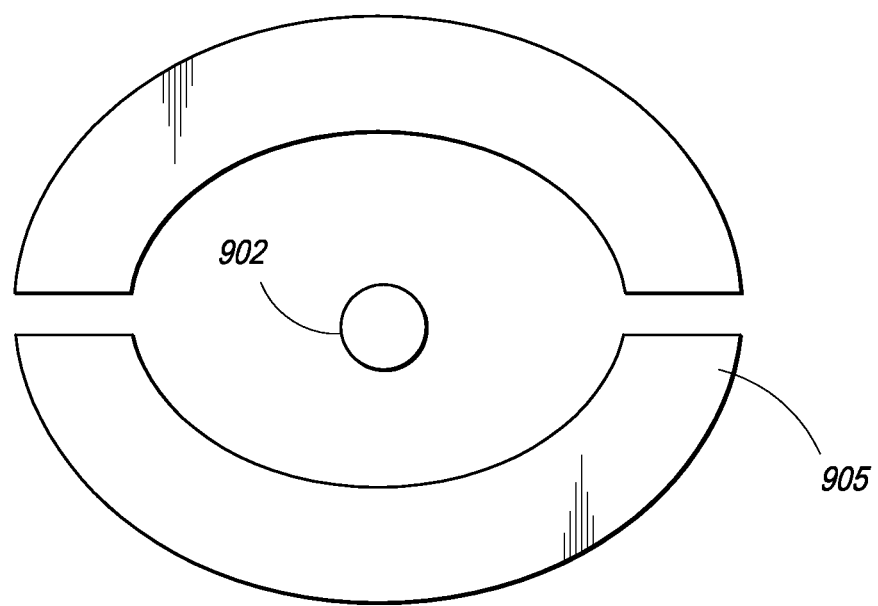
FIG. 9 is an illustration of another embodiment of the present invention.

The above examples are merely illustrative of the many applications of the system of present invention. Other energy sources can be used, including but not limited to radiation-based sources, such as gamma radiation; mm wave, terahertz, and trace-based. For example, FIG. 9 shows a millimeter wave scanner 905 with a shoe scanner 902 integrated into, or proximate to, the center base of the scanner 905. Millimeter waves are transmitted from antennas simultaneously as they rotate around the body. The wave energy reflected back from the body or other objects on the body is used to construct a three-dimensional image, which is displayed on a remote monitor for analysis. In one embodiment, the shoe scanner 902 comprises a mirror or reflective surface positioned in a stationary or rotatory configuration below the scanning position of the individual. In one embodiment, the shoe scanner 902 comprises a millimeter wave scanner in combination with a metal detector.

Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

I claim:

1. A scanning system for screening an individual comprising:
a first system for scanning a body of a person, the first system comprising at least one radiation source for projecting radiation on the body of the person and at least one detector for detecting un-attenuated radiation emerging from the body; and,
a second system for scanning a shoe worn by the person, using said at least one radiation source, further comprising at least one metal detector coil for detecting metals within the shoe and at least one detector for detecting radiation transmitted through the shoe, wherein data from said first system and said second system, including said at least one metal detector coil, are combined to produce a radiographic image of the person and the shoe.

2. The system of claim 1 wherein said radiation source on said system for scanning a shoe further comprises an X-ray source for projecting a beam of X-rays onto the shoe.

3. The system of claim 1 wherein said detector for transmitting radiation transmitted through the shoe comprises a linear detector array for detecting radiation transmitted through the shoe, the detector array moving on a predefined path, wherein the motion of the detector array is synchronized with the motion of the radiation source.

4. The system as claimed in claim 2 wherein the X-ray source is at least one of a single-energy source, a dual-energy source or a spectroscopic transmission source.

5. The system as claimed in claim 2 wherein the X-ray source rotates in accordance with a predefined angle.

6. The system as claimed in claim 2 wherein the X-ray source is stationary.

7. The system as claimed in claim 3 wherein the linear detector array moves along a predefined path for capturing radiation transmitted through the shoe, wherein the predefined path covers one or more sides of the shoe.

8. The system as claimed in claim 2 wherein the X-ray source projects a cone beam of X-rays onto the shoe, wherein X-rays transmitted through the shoe are detected by at least one X-ray area detector for producing a radiographic image of the shoe in a single scan.

9. The system as claimed in claim 2 wherein the X-ray source projects a pencil beam of X-rays onto the shoe, wherein X-rays transmitted through the shoe are detected by at least one X-ray area detector for producing a radiographic image of the shoe.

10. The system as claimed in claim 1 wherein the radiographic image is presented to an operator on a display for analysis.

11. The system as claimed in claim 10 wherein the radiographic image is used to generate automated alarms.

12. The system of claim 1, wherein the second system is a millimeter wave based scanning system.

* * * * *